United States Patent
Ruhl et al.

(10) Patent No.: US 9,568,447 B2
(45) Date of Patent: Feb. 14, 2017

(54) FLUID SENSOR CHIP AND METHOD FOR MANUFACTURING THE SAME

(71) Applicant: Infineon Technologies AG, Neubiberg (DE)

(72) Inventors: Guenther Ruhl, Regensburg (DE); Florian Bachl, Regensburg (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 0 days.

(21) Appl. No.: 15/136,047

(22) Filed: Apr. 22, 2016

(65) Prior Publication Data
US 2016/0238549 A1 Aug. 18, 2016

Related U.S. Application Data

(62) Division of application No. 14/143,634, filed on Dec. 30, 2013, now Pat. No. 9,347,911.

(51) Int. Cl.
*G01N 27/12* (2006.01)
*G01N 27/403* (2006.01)
*G01N 33/00* (2006.01)
*H01L 51/00* (2006.01)

(52) U.S. Cl.
CPC .......... *G01N 27/127* (2013.01); *G01N 27/125* (2013.01); *G01N 27/403* (2013.01); *G01N 33/0027* (2013.01); *H01L 51/0003* (2013.01); *H01L 51/0021* (2013.01)

(58) Field of Classification Search
CPC G01N 27/127; G01N 27/403; G01N 27/4146; G01N 27/4141; H01L 51/0045; H01L 51/0048; H01L 23/53276; Y10S 977/742
See application file for complete search history.

(56) References Cited

U.S. PATENT DOCUMENTS

| | | | |
|---|---|---|---|
| 5,880,552 A | 3/1999 | McGill et al. | |
| 7,015,142 B2 | 3/2006 | DeHeer et al. | |
| 2009/0155561 A1 | 6/2009 | Choi et al. | |
| 2011/0057168 A1 | 3/2011 | Kobayashi | |
| 2011/0206934 A1 | 8/2011 | Bol et al. | |
| 2013/0015583 A1 | 1/2013 | Hoeckele | |
| 2013/0018599 A1 | 1/2013 | Peng | |
| 2013/0091929 A1 | 4/2013 | Lee et al. | |

FOREIGN PATENT DOCUMENTS

| | | |
|---|---|---|
| EP | 2055673 A1 | 5/2009 |
| JP | 2011169634 A | 1/2011 |
| KR | 1020110039803 A | 4/2011 |
| WO | 2010096646 A2 | 8/2010 |
| WO | 2012150884 A1 | 11/2012 |

OTHER PUBLICATIONS

F. Schedin, et al. "Detection of Individual Gas Molecules Absorbed on Graphene" Nature Materials 6 Published 2007.

(Continued)

*Primary Examiner* — Tucker J Wright
(74) *Attorney, Agent, or Firm* — Eschweiler & Associates, LLC

(57) ABSTRACT

A fluid sensor chip includes an isolator substrate including amorphous carbon, an electrical conductor including graphite and an active material including graphene or carbon nanotubes.

9 Claims, 2 Drawing Sheets

(56) References Cited

OTHER PUBLICATIONS

J.D. Fowler, et al. "Practical Chemical Sensors from Chemically Derived Graphene" ACS Nano, vol. 3 Published 2009.
J. T. Robinson, et al. "Reduced Graphene Oxide Molecular Sensors" Nano Letters vol. 8, No. 10 Published 2008.
S. Stankovich, et al. "Synthesis of Graphene-Based Nanosheets via Chemical Reduction of Exfoliated Graphite Oxide" Carbon 45 Published 2007.
D. Li, et al. "Processable Aqueous Dispersions of Graphene Nanosheets" Nature Nanothechnology vol. 3 Published 2008.
X. Li, et al. "Large-Area Synthesis of High-Quality and Uniform Graphene Films on Copper Foils" Science 324 Published 2009.
Z. Sun, et al. "Growth of Graphene from Solid Carbon Sources" Nature 468 Published 2010.
K.S. Kim, et al. "Large-Scale Pattern Growth of Graphene Films for Stretchable Transparent Electrodes" Nature 457 Published 2008.
Notice of Allowance Dated Feb. 2, 2016, U.S. Appl. No. 14/143,634.
Non-Final Office Action Dated Jul. 27, 2015, U.S. Appl. No. 14/143,634.

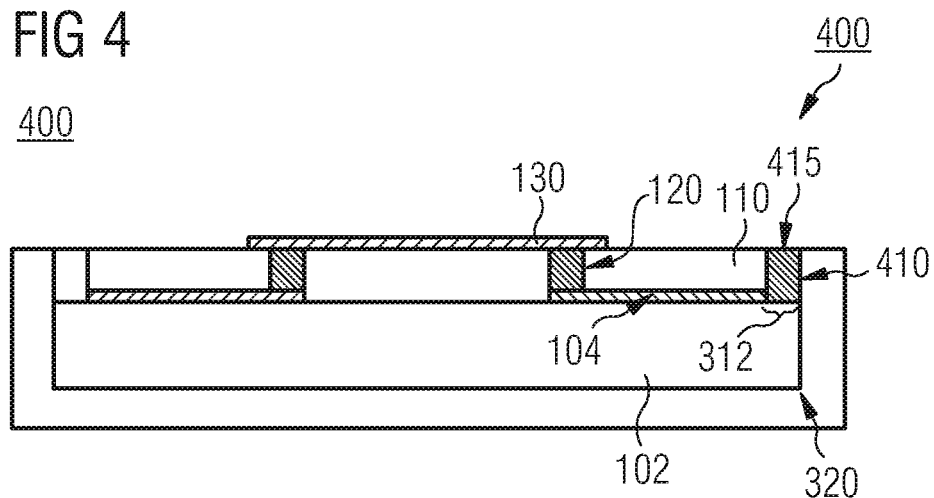
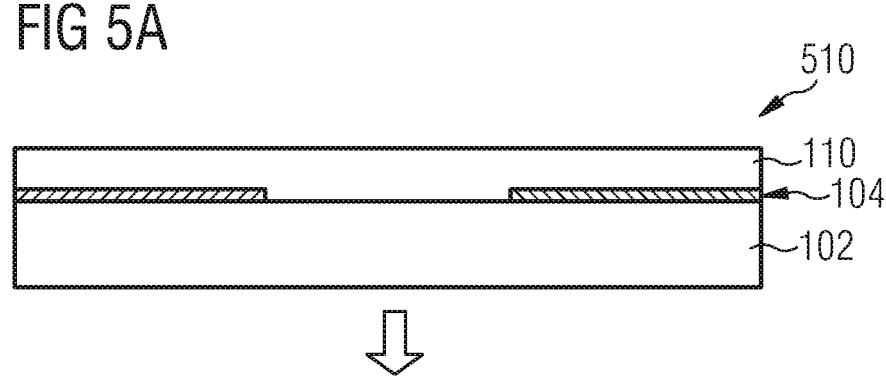
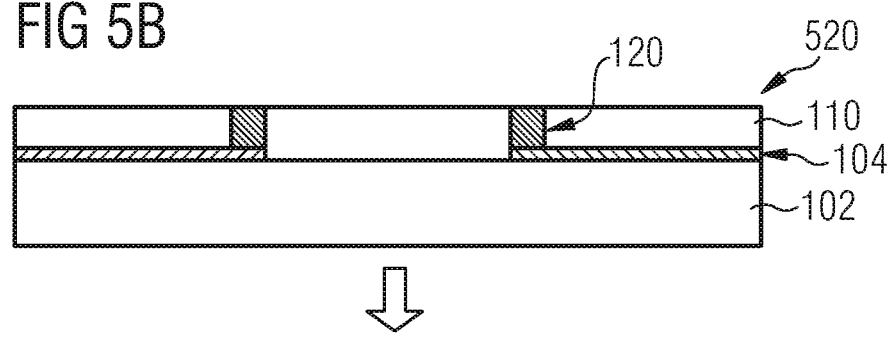
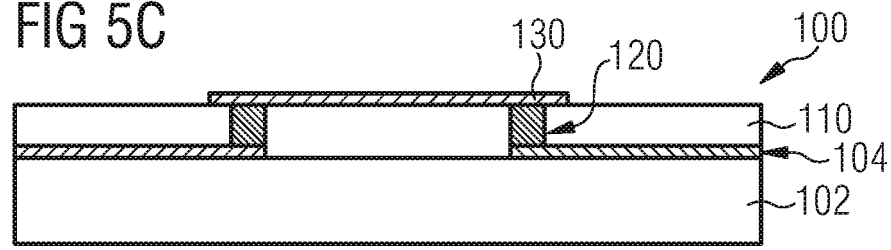

# FLUID SENSOR CHIP AND METHOD FOR MANUFACTURING THE SAME

REFERENCE TO RELATED APPLICATION

This application is a Divisional of U.S. application Ser. No. 14/143,634 filed on Dec. 30, 2013, the contents of which are incorporated by reference in their entirety.

FIELD

Embodiments relate to a fluid sensor chip. Some embodiments relate to a method for manufacturing a fluid sensor chip.

BACKGROUND

Chemical sensors such as gas sensors, for example, in many cases consist of materials which are not chemically inert. On the one hand, the metal or Si substrates and the metal conductors, and on the other hand the active sensor layers such as metal oxides, for example, are attacked by aggressive chemicals (e.g. acids, HF, etc.). One site of application having such a chemically aggressive environment is the interior of an Li ion battery cell. Here, e.g. the electrolyte consists of fluorine-containing conducting salts dissolved in organic solvents (typically carbon dioxide esters).

SUMMARY

A fluid sensor chip is provided. The fluid sensor chip comprises an isolator substrate comprising amorphous carbon, an electrical conductor comprising graphite and an active material comprising graphene or carbon nanotubes.

A further fluid sensor chip is provided. The further fluid sensor chip comprises a substrate carrier, a conductive layer, an isolator substrate comprising amorphous carbon, an electrical conductor comprising graphite and an active material comprising graphene or carbon nanotubes. The conductive layer is arranged between the isolator substrate and the substrate carrier. The isolator substrate is formed above the substrate carrier and the conductive layer. The active material is formed above the conductive layer and the isolator substrate. The electrical conductor extends from the active material to the conductive layer through the isolator substrate, to electrically connect the active material with the conductive layer.

A fluid sensor chip for sensing a physical or chemical parameter in a chemically aggressive environment is provided. Here, all sensor chip surfaces exposed to the chemically aggressive environment comprise or consist of chemically inert carbon.

A method for manufacturing a fluid sensor chip is provided. The method comprises providing a substrate carrier, providing a conductive layer on the substrate carrier, forming an isolator substrate comprising amorphous carbon above the substrate carrier and the conductive layer, providing an electrical conductor comprising graphite, such that the electrical conductor extends through the isolator substrate and contacts the conductive layer, and depositing an active material comprising graphene or carbon nanotubes onto the isolator substrate and the electrical conductor.

BRIEF DESCRIPTION OF THE DRAWINGS

FIG. 4 shows a schematic cross-sectional view of a fluid sensor chip comprising an electrically conductive portion comprising metal; and FIGS. 5a to 5c show schematic cross-sectional views of different components of a fluid sensor chip illustrating a method for manufacturing the same.

DETAILED DESCRIPTION

Figure 1:
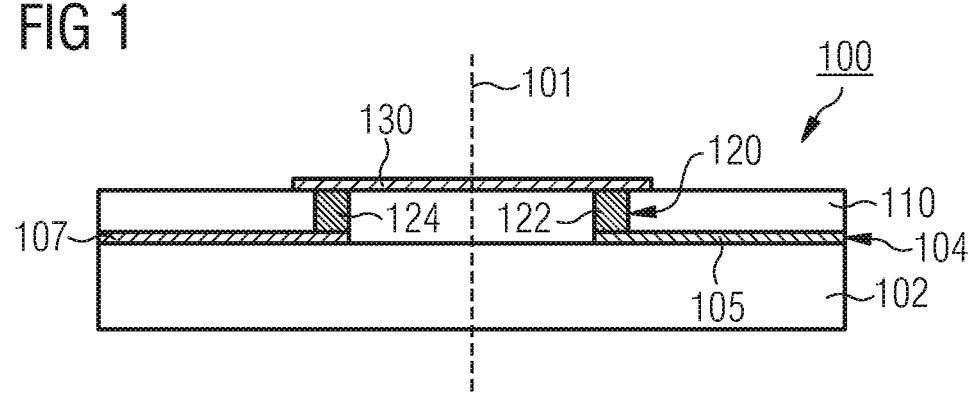
FIG. 1 shows a schematic cross-sectional view of a fluid sensor chip.

Before discussing the present disclosure in further detail using the drawings, it is pointed out that in the figures, identical elements, elements having the same function or the same effect are provided with the same reference numerals so that the description of these elements and the functionality thereof illustrated in the different embodiments is mutually exchangeable or may be applied to one another in the different embodiments.

In conventional chemical sensors, implementing substrates and contact wires in noble metals may protect them from chemical attacks. However, this entails higher manufacturing cost. It is also possible to coat the substrates and contact wires with polymers; however, they are often not resistant to organic solvents. Protection of the active layers may be achieved, to a limited extent, only by using partially permeable membranes. However, as a result, the sensitivity and the response and regeneration times typically increase.

Therefore, a need exists for an improved concept of a fluid sensor chip, which can reliably be used, even in a chemically aggressive environment.

Embodiments of the disclosure provide a comparatively robust sensor chip that can be achieved if an isolator substrate comprising amorphous carbon is formed above a substrate carrier and a conductive layer, if an electrical conductor comprising graphite is provided, such that the electrical conductor extends through the isolator substrate and contacts the conductive layer, and if an active material comprising graphene or carbon nanotubes is deposited onto the isolator substrate and the electrical conductor. In this way, the disadvantage that the sensor chip or its components is/are not sufficiently protected against the surrounding aggressive chemicals (e.g. acids, HF, etc.) can substantially be avoided.

FIG. 1 shows a schematic cross-sectional view of a fluid sensor chip 100. As shown in the example of FIG. 1, the fluid sensor chip 100 comprises an isolator substrate 110 comprising amorphous carbon, an electrical conductor 120 comprising graphite and an active material 130 comprising graphene or carbon nanotubes.

It is depicted as one example in FIG. 1 that the fluid sensor chip 100 may also comprise a substrate carrier 102 (or wafer substrate) and a conductive layer 104.

For example, the isolator substrate 110 may represent a layer of the fluid sensor chip 100. In addition, the isolator substrate or layer 110 may be arranged on top of a substrate (i.e. the substrate carrier 102) made from another material.

The fluid sensor chip of FIG. 1 provides the advantage that it is relatively robust and can reliably be used, even in a chemically aggressive environment. This substantially allows for a more flexible and/or reliable use of the fluid sensor chip.

As shown in one example in FIG. 1, the fluid sensor chip 100 may comprise a substrate carrier 102. In addition, the fluid sensor chip 100 may comprise a conductive layer 104, an isolator substrate 110 comprising amorphous carbon, an electrical conductor 120 comprising graphite and an active material 130 comprising graphene or carbon nanotubes. For example, the conductive layer 104 may be arranged between the isolator substrate 110 and the substrate carrier 102. In addition, the isolator substrate 110 may be formed above the substrate carrier 102 and the conductive layer 104. Furthermore, the active material 130 may be formed above the conductive layer 104 and the isolator substrate 110. It can be seen from FIG. 1 that the electrical conductor 120 may extend from the active material 130 to the conductive layer 104 through the isolator substrate 110, to electrically connect the active material 130 with the conductive layer 104.

The structure of the sensor chip shown as one example in FIG. 1 substantially represents a robust sensor chip which is suitable for the use in a chemically aggressive environment. The presented sensor chip allows for reliably sensing a physical or chemical parameter of a fluid such as a gas or a liquid.

Figure 2:
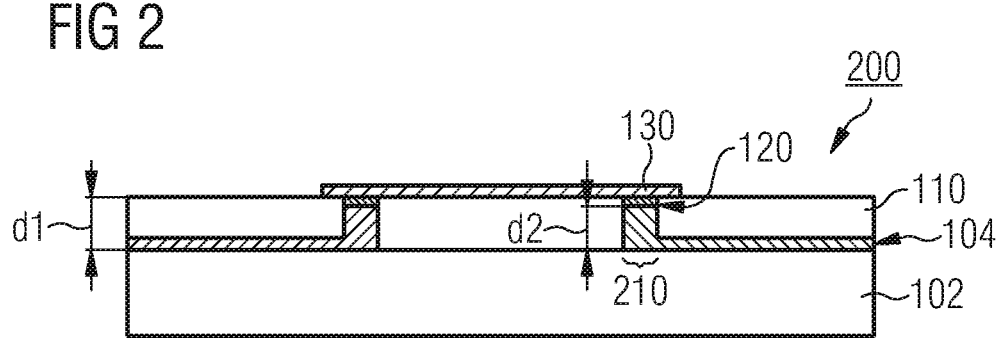
FIG. 2 shows a schematic cross-sectional view of an alternative implementation of a fluid sensor chip.

FIG. 2 shows a schematic cross-sectional view of an alternative implementation of a fluid sensor chip 200. The fluid sensor chip 200 shown as one example in FIG. 2 essentially corresponds to the fluid sensor chip 100 shown in FIG. 1. Therefore, a repeated description of corresponding or identical components is omitted. However, as opposed to the fluid sensor chip 100 shown in FIG. 1, the conductive layer 104 of the fluid sensor chip 200 shown as one example in FIG. 2 may be formed differently. For example, in a region 210 below the electrical conductor 120, the conductive layer 104 may extend through the isolator substrate 110, wherein an extension d2 of the conductive layer 104 through the isolator substrate 110 may be larger than half of the width d1 of the isolator substrate 110. However, as in the structure of the fluid sensor chip 100 of FIG. 1, the electrical conductor 120 of the fluid sensor chip 200 in FIG. 2 may extend from the active material 130 to the conductive layer 104 through the isolator substrate 110, to electrically connect the active material 130 with the conductive layer 104.

Figure 3:
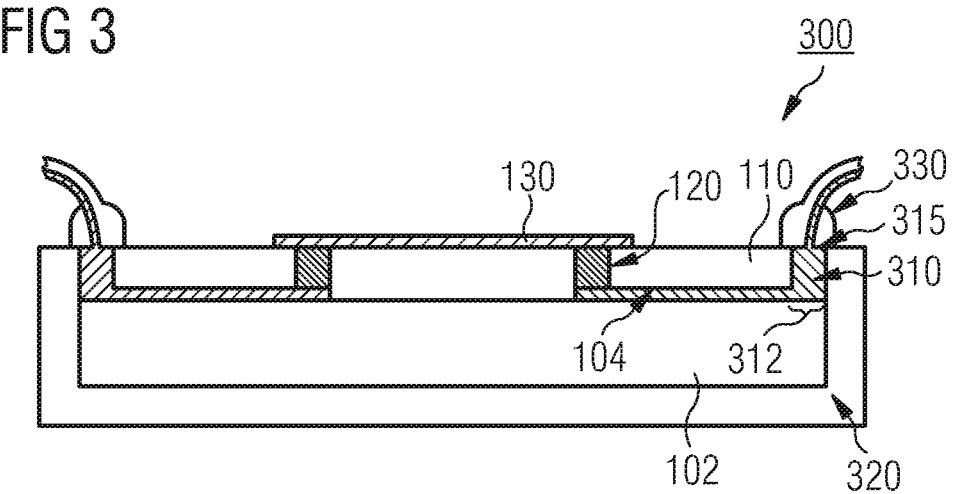
FIG. 3 shows a schematic cross-sectional view of a fully encapsulated implementation of a fluid sensor chip comprising an electrically conductive portion comprising graphite.

FIG. 3 shows a schematic cross-sectional view of a fully encapsulated implementation of a fluid sensor chip 300 comprising an electrically conductive portion 310 comprising graphite. The fluid sensor chip 300 shown as one example in FIG. 3 essentially corresponds to the fluid sensor chip 100 shown in FIG. 1. Therefore, a repeated description of corresponding or identical components is omitted. However, the fluid sensor chip 300 of FIG. 3 may comprise an electrically conductive portion 310 extending through the isolator substrate 110, wherein the electrically conductive portion 310 may be configured to couple an external electrical contact 315 of the fluid sensor chip 300 with the conductive layer 104. Referring to FIG. 3 as one example, the electrically conductive portion 310 may be arranged in a border region 312 of the fluid sensor chip 300.

As shown as one example in FIG. 3, the fluid sensor chip 300 may further comprise a sealing 320 configured to seal the substrate carrier 102.

For example, the sealing 320 may comprise amorphous carbon or consist of amorphous carbon. By providing such a sealing, it is possible to substantially protect the substrate carrier 102 of the fluid sensor chip 300 against a chemically aggressive fluid medium, such as a gaseous or liquid medium.

In addition, the sealing 320 in one embodiment may cover all surfaces of the sensor chip 300, except for the active material 130 and external electrical contacts 315. This has the advantage that the improved sensor chip can be provided which is also suited for the application in a chemically aggressive environment (e.g. in the interior of an Li ion battery cell).

For example, the electrically conductive portion 310 comprises a metal (e.g. Cu). In addition, the fluid sensor chip 300 may further comprise an insulating portion 330 configured to insulate the electrically conductive portion 310 comprising the metal. In this way, the metallic, electrically conductive portion 310 can also be covered, such that the external electrical contact 315 of the fluid sensor chip will be protected.

FIG. 4 shows a schematic cross-sectional view of a fluid sensor chip 400 comprising an electrically conductive portion 410 comprising graphite. The fluid sensor chip 400 comprising the components 102, 104, 110, 120 and 130 are shown in one example in FIG. 4 essentially corresponds to the fluid sensor chip 100 comprising the elements 102, 104, 110, 120 and 130 shown in FIG. 1. Therefore, a repeated description of corresponding or identical elements is omitted. In the example of FIG. 4, the electrically conductive portion 410 may comprise graphite. Since the electrically conductive portion 410 of the fluid sensor chip 400 may comprise graphite, an insulating portion configured to insulate the electrically conductive portion 410 is not required. Rather, the electrically conductive portion 410 comprising graphite is already resistant to the chemically aggressive environment.

For example, the fluid sensor chip 100 may be a sensor chip for sensing a physical or chemical parameter of a gas or a liquid. In other words, the sensor chip may be used as a gas sensor or a liquid sensor in a chemically aggressive environment.

For example, the fluid sensor chip shown as examples in FIGS. 1 to 4 is configured for sensing a physical or chemical parameter in a chemically aggressive environment, wherein all sensor chip surfaces exposed to the chemically aggressive environment comprise or consist of chemically inert carbon.

Referring to the previous examples of the fluid sensor chip, the electrical conductor 120 may comprise two distinguished electrical conductor portions 122, 124 symmetrically arranged with respect to a central, vertical axis 101 of the fluid sensor chip 100, such that the active material 130 can be electrically connected with the conductive layer 104 by the two distinguished electrical conductor portions 122, 124. In addition, two distinguished conductive layer portions 105, 107 of the conductive layer 104 may be separated by the isolator substrate 110 in a central region of the fluid sensor chip around the central, vertical axis 101.

FIGS. 5a to 5c show schematic cross-sectional views of different components 510, 520 of a fluid sensor chip 100 illustrating a method for manufacturing the same. For example, a method for manufacturing a fluid sensor chip may comprise the following acts. First, a substrate carrier 102 may be provided. Then, a conductive layer 104 may be provided on the substrate carrier 102. Then, an isolator substrate 110 comprising amorphous carbon may be formed above the substrate carrier 102 and the conductive layer 104. Then, an electrical conductor 120 comprising graphite may be provided, such that the electrical conductor 120 extends through the isolator substrate 110 and contacts the conductive layer 104. Finally, an active material 130 comprising graphene or carbon nanotubes may be deposited onto the isolator substrate 110 and the electrical conductor 120.

Accordingly, FIG. 5a shows the result or component 510 after the act of providing the substrate carrier 102, the act of providing and patterning the conductive layer 104 and the act of forming the isolator substrate 110. In addition, FIG. 5b depicts as one example the result or component 520 after the act of providing the electrical conductor 120 in the isolator substrate 110. Finally, FIG. 5c depicts as one example the result or fluid sensor chip 100 after the act of depositing the active material 130.

For example, the isolator substrate 110 may comprise or consist of amorphous carbon. In addition, the electrical conductor 120 may comprise or consist of graphite. Furthermore, the active material 130 may comprise or consist of graphene.

Additionally or alternatively, the active material 130 may be selected from a group consisting of graphene, functionalized graphene, covalently functionalized graphene, graphene functionalized with a metal and graphene functionalized with metal oxides or other metal chalcogenides. The functionalizing compounds can be in the form of continuous films as well as in the form of particles, for example, nanoparticles.

Regarding the manufacturing method, the same may further comprise encapsulating the substrate carrier 102. In this way, a housing or sealing (e.g. the sealing 320) may be provided for the fluid sensor chip.

For example, the act of forming the isolator substrate 110 may comprise performing a plasma based chemical vapor deposition from gaseous hydrocarbons onto the substrate carrier 102.

In addition, the act of providing the electrical conductor 120 may comprise performing a spatially localized thermal irradiation of the isolator substrate 110, wherein the amorphous carbon of the isolator substrate 110 is converted into graphite.

Here, in one embodiment the thermal irradiation of the isolator substrate 110 may be performed by a laser irradiation or the exposure of light using a projection mask.

Furthermore, the act of depositing the active material 130 may comprise applying and drying off a graphene suspension or a graphene oxide suspension and heating it to a temperature between about 300° C. and 900° C. or a suspension of functionalized graphene or transferring graphene layers previously deposited onto a temporary substrate.

For example, the act of depositing the active material 130 comprises depositing nanoparticles (e.g. in a suspension) onto graphene previously deposited onto a temporary substrate and transferring the previously deposited graphene to the fluid sensor chip.

In addition, the act of depositing the active material 130 may comprise depositing graphene onto the isolator substrate 110 and subsequently depositing nanoparticles onto the graphene (e.g. by an electrochemical deposition).

In summary, the fluid sensor chip provides the advantage that it is possible to implement a gas sensor, for example, wherein the surfaces exposed to the surrounding media comprise or consist exclusively of chemically inert carbon. For example, the fluid sensor chip is based on a combination of amorphous carbon for the insulator substrate, graphite for the electrical conductor and graphene for the active material.

In the act of forming the isolator substrate or in the step of encapsulating the substrate carrier, amorphous carbon may be used. Thus, amorphous carbon may be used for coating the substrate carrier 102. The isolator substrate 110 or sealing 320 comprising amorphous carbon may be produced by means of plasma-supported chemical vapor deposition from gaseous hydrocarbons. Here, it is pointed out that amorphous carbon is inert to practically any chemicals, except for oxygen plasma and oxygen at temperatures above 500° C., and it entails low manufacturing costs. A general feature of amorphous carbon is that it is electrically insulating and may be employed as a dielectric in electronic components such as in a gas sensor, for example. Advantageously, amorphous carbon can be used in the fluid sensor chip according to the present disclosure.

In the act of providing the electrical conductor 120, graphite may be used. In general, graphite has the same chemical resistance as amorphous carbon, but is an electrical conductor. For example, graphite may be produced from amorphous carbon by means of a thermal treatment. The formation of graphite may also be performed in a localized manner, e.g. by means of laser irradiation, such as described in DE 10 2012 212 152 A1. Thus, it is possible to form the electrical conductor 120 or electrically conductive graphite structures in an insulating matrix comprising or consisting of amorphous carbon. For example, the absorption of the laser irradiation may be varied by selecting the laser wavelength and the adjustment of the absorption coefficient of the amorphous carbon layer (or the isolator substrate 110), e.g. by doping the isolator substrate 110 with a few atom percent of nitrogen. Thus, the depth of the electrical conductor 120 extending through the isolator substrate 110 or graphitic conversion zone may also be adjusted.

In the act of depositing the active material 130 of the fluid sensor chip, graphene may be used. In general, graphene is a new type of material which may serve, among other things, as the active material for producing gas sensors, such as described in KR 102011039803 A and JP 002011169634 A. The principle of measurement employed by the fluid sensor chip substantially corresponds to a change in the resistance of the active material 130 or graphene layer upon adsorption of gas molecules. Such a principle is also described in F. Schedin et al., Detection of Individual Gas Molecules Adsorbed on Graphene, Nature Materials 6 (2007) 652; J. D. Fowler et al., Practical Chemical Sensors from Chemically Derived Graphene, ACS Nano, 3 (2009) 301; and J. T. Robinson et al., Reduced Graphene Oxide Molecular Sensors, Nano Lett. 8 (2008) 3137.

As a carbon modification, graphene also has the same chemical resistance as amorphous carbon. This material may be produced at low cost from graphite or hydrocarbon gases.

Basically, an implementation of a gas sensor has been found, wherein the surface exposed to the surrounding media may comprise or consist of chemically resistant carbon.

For example, the fluid sensor chip may be manufactured as follows. First, an electrically insulating amorphous carbon (e.g. having a thickness of 10 to 5000 nm) may be deposited onto a substrate (or the substrate carrier 102) comprising electrical contacts (or the conductive layer 104) for connecting the active layer (or the active material 130). For improving the laser absorption, the amorphous carbon may also contain some atom percent of nitrogen. At the regions located above the electrical contacts or electrodes for the active layer (i.e. above the electrical conductor 120), the isolator substrate 110 comprising amorphous carbon may be locally converted into conductive graphite (e.g. having a resistivity of $\rho=0.5-50$ m$\Omega$·cm) by means of a laser annealing act at a locally produced temperature of about 700 to about 1500° C. Local introduction of the temperature required may also be effected by the exposure to light of, e.g., xenon lamps and a projection mask. The graphite contact (or the electrical conductor 120) may be configured as a complete via on a metal conductor trace or as a resist layer on a metal via. A graphene layer (or the active material 130) may be applied as an active sensor layer onto and between said graphite contacts. Possible deposition processes for applying the active material 130 include applying and drying off and/or baking a graphene or graphene oxide suspension as well as transferring graphene layers deposited onto a temporary substrate.

The graphene layer or the active material 130 may be produced in the following ways. For example, reduced graphene oxide, such as described in S. Stankovich et al., Synthesis of graphene-based nanosheets via chemical reduction of exfoliated graphite oxide, Carbon 45 (2007) 1558, and D. Li et al., Processable aqueous dispersions of graphene nanosheets, Nature Nanotechnology 3 (2008) 101, can be employed. In addition, graphene CVD, such as described in X. Li et al., Large-Area Synthesis of High-Quality and Uniform Graphene Films on Copper Foils, Science 324 (2009) 131, EP 000002055673 A, US 020090155561 A, can be employed. Furthermore, solid-state sources, such as described in US 020110206934 A, and Z. Sun et al., Growth of graphene from solid carbon sources, Nature 468 (2010) 549, can be employed. Finally, a solid-state epitaxy such as described in U.S. Pat. No. 7,015,142 B and WO 002010096646 A may be applicable.

Besides this, the methods of using graphene CVD, solid-state sources or solid-state epitaxy may be employed in connection with a transfer process onto the desired substrate, such as described in K. S. Kim et al., Large-scale pattern growth of graphene films for stretchable transparent electrodes, Nature 457 (2008) 706 and EP 000002055673 A.

For example, the graphene layer or the active material 130 may also comprise or consist of functionalized graphene, i.e. of chemically modified graphene or graphene having a decoration or continuous layer consisting of a different material (e.g. metal nanoparticles), so as to create selectivity for specific atoms, molecules or ions. The functionalization of graphene may be performed prior to or following application onto the sensor substrate.

In general, the fluid sensor chip may be employed as a chemical sensor, i.e. both in gases and in liquids.

In the following, different example materials which may serve as a chemically inert sensor material or as the active material 130 in the fluid sensor chip will be discussed.

For example, non-functionalized graphene may be used. In this case, selectivity will be limited. Electron donors (e.g. NH3) lead to an increase in the layer resistance by changing the charge carrier density in the graphene, while electron acceptors lead to a decrease in the layer resistance. Adsorbates which do not change the charge carrier density in the graphene (e.g. noble gases) do not result in any sensor response. For some applications, such a limited selectivity may suffice, for example, if nothing but changes in concentration are to be detected.

In addition, covalently functionalized graphene may be used. In this case, functional groups (e.g. —OH, —H, —F, —NH2, etc.) which in one embodiment bind the desired analyte molecules and influence the charge carrier density in the graphene are bound to the graphene. Here, functionalization may have to be adapted to the medium since the functional groups are possibly not resistant to all possible surrounding media.

Furthermore, graphene functionalized with noble metal (nanoparticles, film) may be used. Here, the desired analyte molecules (e.g. H2) are adsorbed or absorbed by the noble metal (e.g. Au, Pt, Pd), which decorates the graphene, and changes the charge carrier density in the graphene, e.g. by changing the work function of the metal. Due to its noble-metal character, this functionalization is chemically resistant.

Finally, other functionalizations may be used. However, these other functionalizations, such as metal oxides (e.g. TiO2, MnO2, etc.), for example, are generally chemically resistant in specific media only. Here, a major influencing factor is the pH value. However, for a limited selection of media, the functionalizations may also be used for the chemically highly resistant sensor.

The present disclosure is beneficial in that a corrosion-resistant gas sensor may be provided, which can reliably be used in a chemically aggressive environment.

Although some aspects have been described in the context of an apparatus, it is clear that these aspects also represent a description of the corresponding method, where a block or device corresponds to a method act or a feature of a method act. Analogously, aspects described in the context of a method act also represent a description of a corresponding block, or item or feature of a corresponding apparatus.

The above described embodiments are merely illustrative for the principles of the present disclosure. It is understood that modifications and variations of the arrangements and the details described herein will be apparent to others skilled in the art. It is the intent, therefore, to be limited only by the scope of the appending patent claims and not by the specific details presented by way of description and explanation of the embodiments herein.

The invention claimed is:

1. A method for manufacturing a fluid sensor chip, comprising:
   providing a substrate carrier;
   providing a conductive layer on the substrate carrier;
   forming an isolator substrate comprising amorphous carbon above the substrate carrier and the conductive layer;
   providing an electrical conductor comprising graphite, such that the electrical conductor extends through the isolator substrate and contacts the conductive layer; and
   depositing an active material comprising graphene or carbon nanotubes onto the isolator substrate and the electrical conductor.

2. The method according to claim 1, further comprising encapsulating the substrate carrier.

3. The method according to claim 1, wherein forming the isolator substrate comprises performing a plasma based chemical vapor deposition of gaseous hydrocarbons onto the substrate carrier.

4. The method according to claim 1, wherein providing the electrical conductor comprises performing a spatially localized thermal irradiation of the isolator substrate, wherein the amorphous carbon of the isolator substrate is converted into graphite.

5. The method according to claim 4, wherein a depth of the electrical conductor extending through the isolator substrate is adjusted by doping the isolator substrate with at most 5 atom percent of nitrogen.

6. The method according to claim 4, wherein performing the spatially localized thermal irradiation comprises a local introduction of a temperature by exposing the isolator substrate to light of a xenon lamp using a projection mask.

7. The method according to claim 1, wherein depositing the active material comprises applying and drying off a graphene suspension or a graphene oxide suspension or transferring graphene layers previously deposited onto a temporary substrate.

8. The method according to claim 1, wherein depositing the active material comprises depositing nanoparticles onto graphene previously deposited onto a temporary substrate and transferring the previously deposited graphene to the fluid sensor chip.

9. The method according to claim 1, wherein depositing the active material comprises depositing graphene onto the isolator substrate and subsequently depositing nanoparticles onto the graphene.

* * * * *